(12) United States Patent
Argauer et al.

(10) Patent No.: US 9,522,227 B2
(45) Date of Patent: Dec. 20, 2016

(54) MANUFACTURING METHOD A STRUCTURAL PART WITH A CANNULA, A CANNULA, A STRUCTURAL PART, AN INSERTION HEAD AND AN INSERTION DEVICE WITH THE CANNULA

(75) Inventors: Herbert Argauer, Pirk (DE); Josef Hartinger, Wernberg-Koblitz (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1060 days.

(21) Appl. No.: 13/557,798

(22) Filed: Jul. 25, 2012

(65) Prior Publication Data

US 2012/0296290 A1 Nov. 22, 2012

Related U.S. Application Data

(63) Continuation of application No. PCT/EP2011/050777, filed on Jan. 20, 2011.

(30) Foreign Application Priority Data

Jan. 25, 2010 (DE) ...................... 10 2010 005 6995

(51) Int. Cl.
*A61M 5/158* (2006.01)
*A61M 25/00* (2006.01)
*A61M 25/06* (2006.01)

(52) U.S. Cl.
CPC ......... *A61M 5/158* (2013.01); *A61M 25/0014* (2013.01); *A61M 25/0662* (2013.01); *A61M 2005/1581* (2013.01); *A61M 2005/1585* (2013.01); *A61M 2005/1587* (2013.01); *A61M 2207/00* (2013.01)

(58) Field of Classification Search
CPC ..................... A61M 2207/00; A61M 2207/10; A61M 25/00; A61M 25/0014; A61M 2005/14252; A61M 25/0606; B29C 45/14; B29C 45/14467; Y10T 29/4998; Y10T 29/49993
See application file for complete search history.

(56) References Cited

U.S. PATENT DOCUMENTS 4,362,156 A 12/1982 Feller, Jr. et al.
6,302,866 B1 * 10/2001 Marggi ............ A61M 25/0097
604/174

(Continued)

FOREIGN PATENT DOCUMENTS

EP 0 956 879 A1 11/1999
EP 1 970 091 A1 9/2008

OTHER PUBLICATIONS

International Search Report related to international application No. PCT/EP2011/050777.

(Continued)

*Primary Examiner* — Christopher Besler
(74) *Attorney, Agent, or Firm* — Dinsmore & Shohl LLP

(57) ABSTRACT

A method for manufacturing a structural part with a cannula for the subcutaneous administration of an active substance is disclosed. A loose cannula is threaded on a piercing means to form a ready-to-use cannula piercing unit and subsequently, a cannula housing is injection-molded onto the cannula. Embodiments for the cannula as well as the structural part, an application part, an insertion head, and an insertion device which includes the cannula are also disclosed.

6 Claims, 4 Drawing Sheets

(56) References Cited

U.S. PATENT DOCUMENTS 7,850,652 B2 12/2010 Liniger et al.
2008/0277926 A1* 11/2008 Inman, Jr. ............. A61M 39/10
285/123.15

OTHER PUBLICATIONS

International Preliminary Report on Patentability related to international application No. PCT/EP2011/050777.

* cited by examiner

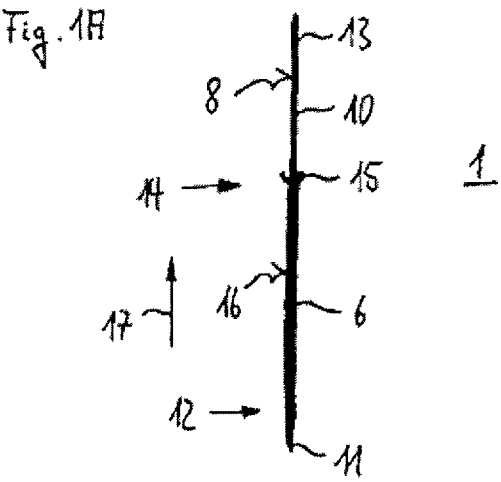
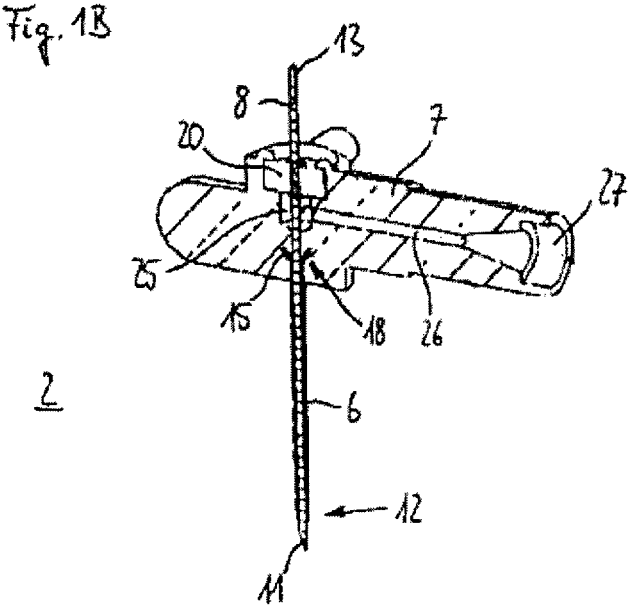

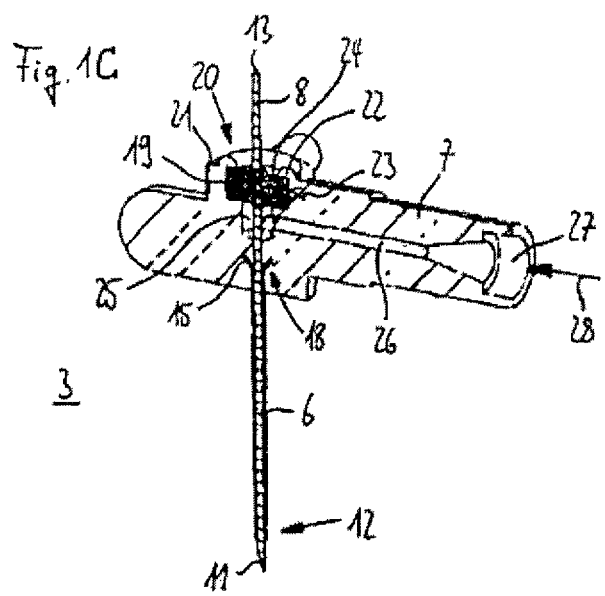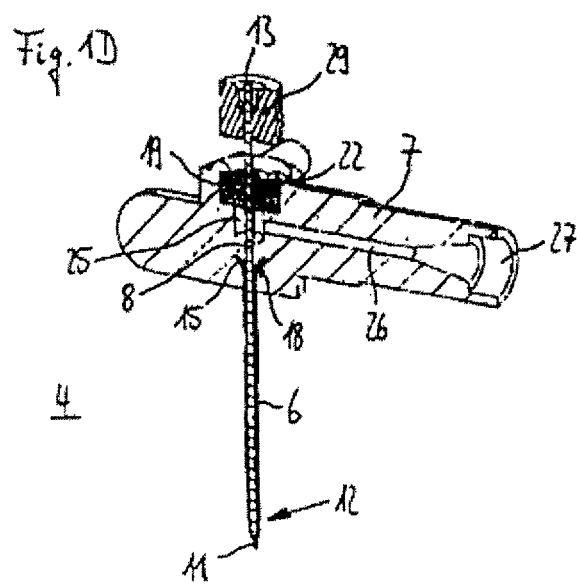

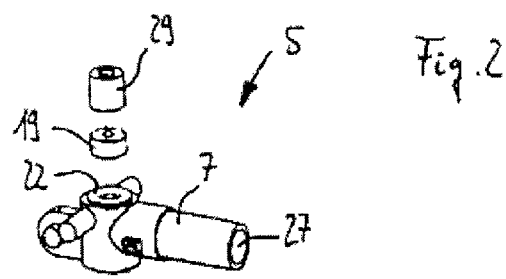
Fig. 2
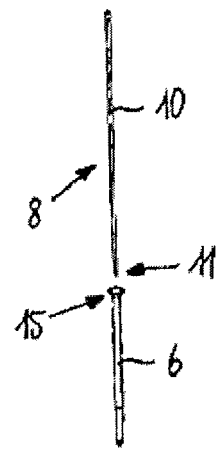
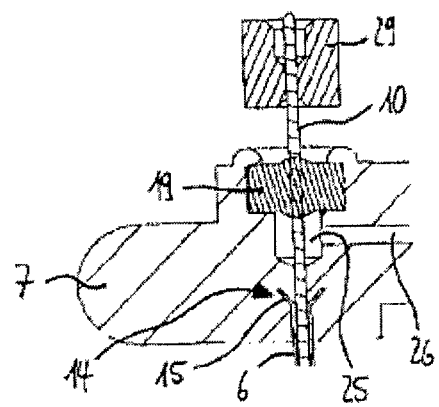
Fig. 3

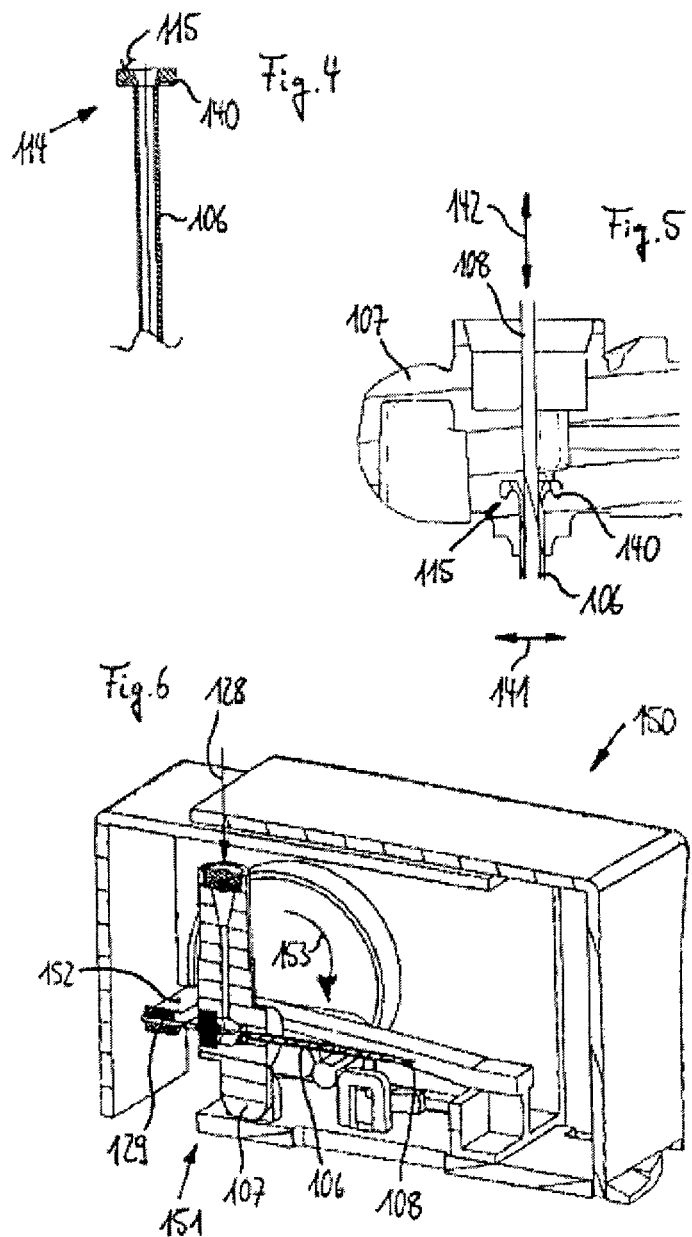

MANUFACTURING METHOD A STRUCTURAL PART WITH A CANNULA, A CANNULA, A STRUCTURAL PART, AN INSERTION HEAD AND AN INSERTION DEVICE WITH THE CANNULA

CROSS-REFERENCE TO RELATED APPLICATIONS

This application is a continuation of International application No. PCT/EP2011/050777, filed Jan. 20, 2011, and which claims priority to German application Serial No. 10 2010 005 6995, filed Jan. 25, 2010.

TECHNICAL FIELD

Disclosed herein are embodiments according to the invention which relate on the one hand to a method for manufacturing a structural part with a cannula for the subcutaneous administration of an active substance, in which the cannula is connected to a cannula housing. On the other hand, other embodiments according to the invention relate to a cannula for a structural part for the subcutaneous administration of an active substance, such as on an application part of an insertion head. Furthermore, still other embodiments according to the invention relate to a structural part with a cannula for the subcutaneous administration of an active substance. Moreover, still further embodiments relate to an insertion head comprising a structural part with a cannula for the subcutaneous administration of an active substance.

BACKGROUND

A generic insertion head comprises a cannula housing in the form of an application part that is applied on the skin, whereby the application part has a piercing device—in the form of a needle—and a flexible introducing device—in the form of a flexible cannula—for an active substance. The piercing device supports the flexible introducing device during the penetration into the skin and it is subsequently drawn out of the flexible introducing device through a septum so that the active substance can be administered through the flexible introducing device in and/or under the skin. The septum is located above the flexible introducing device and it closes the application part after the drawing out of the piercing device at the location at which the latter was previously located.

Such known application parts were previously almost always produced in such a manner that in the first manufacturing step a stabilizing pin is introduced into a flexible cannula in order to be able to better work the flexible cannula during the manufacturing of an associated cannula housing. The structural unit prepared in this manner is then introduced into a previously manufactured cannula housing in order to be able to connect the flexible cannula and the cannula housing to one another by a thermal process in a stable manner. Subsequently, the stabilizing pin is drawn out of the flexible cannula and replaced by the actual piercing means. Damage often occurs to the flexible cannula during the insertion of the piercing means into the flexible cannula of the cannula housing, which unfortunately has the consequence of relatively high rejection rates.

The problem of improving the manufacture and the service life of a generic cannula housing remains a desire.

BRIEF DESCRIPTION OF THE DRAWINGS

In the drawings:

FIG. 1A schematically shows a first manufacturing step of a structural part for the subcutaneous administration of an active substance with a cannula and a cannula housing;

FIG. 1B schematically shows another manufacturing step of a structural part;

FIG. 1C schematically shows another manufacturing step of a structural part;

FIG. 1D schematically shows another manufacturing step of a structural part;

FIG. 2 schematically shows an exploded view of a finished structural part;

FIG. 3 schematically shows a detailed view of a finished structural part;

FIG. 4 schematically shows an alternative embodiment of a cannula;

FIG. 5 schematically shows a detailed view of the cannula from FIG. 4 on a cannula housing; and FIG. 6 schematically shows a view in partial section of an insertion device with a structural part in accordance with an embodiment of the invention for the subcutaneous administration of an active substance.

DETAILED DESCRIPTION

The problem mentioned in the above background is addressed by the various embodiment disclosed herein. For example, in one embodiment a method for manufacturing a structural part with a cannula for the subcutaneous administration of an active substance in which the cannula is connected to a cannula housing is disclosed. The method is distinguished in that a loose cannula is threaded on a piercing means to form a ready-to-use cannula piercing unit and subsequently, a cannula housing is injection-molded onto the cannula.

The above mentioned method embodiment, for example, greatly reduces the danger that the cannula is damaged by the piercing means, as a result of which the rejection rate can be significantly reduced. Also, the above mentioned manufacturing method of the structural part considerably improves the service life of the structural part since injuries to the cannula, which can result in a failure during use, can be avoided. In addition, traditional manufacturing methods can be significantly simplified since in the present embodiments additional manufacturing steps and structural parts, for example, a stabilizing pin, can be eliminated.

In at least one embodiment, the structural part can be designed as an application part that is applied onto a tissue, such as the skin of a patient, where the application part remains for the duration of an administration of an active substance. As the design of such application parts which can be applied onto tissue is already well known from the prior art, no further discussion regarding the same is provided hereafter.

The term "cannula" as used herein is meant to describe every device by which an active substance can be injected. In one embodiment, it may be a flexible mechanism, for example, a soft cannula.

Of course, very different materials can be used for the cannula such as, for example, linear low-density polyethylene (LLDPE), low-density polyethylene (LDPE), high-density polyethylene (HDPR), polytetrafluoroethylene (PTFE), or the like. In one embodiment, fluorinated ethylene propylene (i.e., FEP 100) proved to be suitable since it can slide well into a tissue such as a skin tissue. In one embodiment, the cannula can be constructed in the color white.

The designation "cannula housing" as used herein describes a device that receives the cannula and/or to which the cannula is connected. Such a cannula housing and a cannula may be used in an insertion head as a structural part. A generic insertion head on which such a structural part is used is known from the European patent application EP 1 970 091 A1.

In at least one embodiment of the manufacture of the present cannula housing, the material methyl methacrylate-acrylonitrile-butadiene-styrene (MABS) is used; however, even other thermoplastics can be used such as, for example, polycarbonate (PC), Poly(methyl methacrylate) (PMMA), polypropylene (PP), polyethylene (PE) or the like. In particular, the material MABS is worked in various embodiments of the present manufacturing method at a temperature between 230° C. and 260° C. An additional working of the materials during injection molding can also be achieved if a tool temperature between 50° C. and 80° C. is selected. The injection speed of the material may be between 50 mm/s to 150 mm/s, for example around 100 mm/s.

The active substance to be administered is ideally medicinal liquids.

The piercing means can be any device with which the cannula can be introduced in a supportive manner into a tissue, such as into the skin. To this extent this piercing means remains inside the cannula until the cannula has been brought in an orderly manner into the tissue. Only then is the piercing means withdrawn from the cannula in a known manner. In one embodiment, a needle can be used as a possible piercing means.

The term "cannula piercing unit" as used herein describes a structural group consisting of a cannula and a piercing means, whereby the piercing means is arranged at least partially inside the cannula.

In one embodiment, the cannula can be inserted in a simple and stable manner into an injection-molding tool structurally as well as from an engineering standpoint by the cannula piercing unit in order to subsequently injection-mold a material for the cannula housing around the cannula in such a manner that at least one end of the cannula is firmly embedded in the cannula housing.

A firm connection between the cannula and the cannula housing can be achieved by a positive as well as by a non-positive connection. Cumulatively or alternatively, a connection with the same materials of the cannula and of the cannula housing can also be provided.

Regarding another aspect of the present disclosure, the above mentioned problem is also addressed by a method for manufacturing a structural part with a cannula for the subcutaneous administration of an active substance in which the cannula is connected to a cannula housing, which method is distinguished in that one end of the cannula is formed to an end area that deviates from the shape of the rest of the cannula area, such as from a cylindrical shape and subsequently, a cannula housing is injection-molded on this end area.

In order to connect the cannula to the cannula housing in a manner that is safe in operation, an end area of the cannula may be reshaped in such a manner that it deviates from the shape of the rest of the cannula. In this manner the cannula can be directly provided without other structural parts being required for this step. As a result of the shape which deviates from the shape of the rest of the cannula, the cannula can be anchored extremely firmly in the cannula housing. This is advantageous if the active substance must be injected under pressure as can be the case, for example, with an administration of insulin. To this extent the connection between the cannula and the cannula housing should be able to withstand pressures of up to 4 bar.

In a very simple embodiment, the cannula may have a different diameter in one of its end areas than in the remaining cannula area so that an undercut is formed in particular in the end area of the cannula which undercut can be or is surrounded by the material of the cannula housing.

In this aspect, the above mentioned problem may also addressed by providing a cannula for a structural part for the subcutaneous administration of an active substance on an application part of an insertion head, whereby the cannula has an end area that deviates from the shape of the remaining cannula area. It is already sufficient in this embodiment if the diameter of the end area is greater than a diameter at another position on the cannula. If an end area of the cannula is shaped like a funnel it can already form an undercut sufficiently well that can be surrounded by a material of the cannula housing. To this extent the present cannula can be embedded inseparably in the cannula housing.

A further increasing of the connection strength between the cannula and the cannula housing can be achieved if the funnel-shaped end area comprises a circumferential bead on its side facing away from the cannula which bead shapes a collar on the funnel-shaped end area. With this collar preventing the cannula from sliding out from the cannula housing, securing of the cannula is improved since a good positive connection is ensured.

In another embodiment, such a funnel can also be designed as a circular, polygonal folded-over flange or a flange with some other cross-sectional shape, which flange is completely surrounded with a plastic material of the cannula housing and as a result, generates a firm and tight connection.

In another embodiment, if the end area of the cannula and the remaining cannula area are manufactured from a single material, the present cannula can be distinguished by its simple construction.

Also, regarding the latter method embodiment for the reasons as already explained, if the cannula is threaded on a piercing means to a ready-to-use cannula piercing unit before the injection-molding of the cannula housing such a combination significantly simplifies the manufacture of the initially described application parts.

In another embodiment, a method provides that the cannula housing is injection-molded on the cannula in such a manner that the piercing means movably penetrates the cannula housing. In this manner it can be insured that the piercing means is immediately ready for use.

In a further method step after the injection molding of the cannula housing, a septum element can be inserted on the end side of the piercing means and arranged in a support lug of the cannula housing. The support lug is a chamber of the cannula housing into which the piercing means projects and which can be closed fluid-tight in a simple manner from an engineering standpoint. In one embodiment, the septum element is thermally flanged into the support lug.

It is to be appreciated that the septum element is inserted on or threaded onto the piercing means only after the placing of the piercing means in the cannula. The septum element closes the chamber of the cannula housing immediately in a known manner even during the removal of the piercing means.

In another embodiment, in a next method step of the manufacturing method a holding device is subsequently attached on the end side of the piercing means. The piercing means can be suitably handled mechanically or manually by such a holding device such that it can be readily drawn out of the cannula during the later usage of the structural part.

The holding device can be adhered to the piercing means. For example, the holding device can be fastened to the piercing means by a UV adhesive.

In still another embodiment, a tip of the piercing means together with the outside of the flexible cannula, as long as the piercing means is still in the flexible cannula, can be provided with a layer of silicone in order to improve sliding, such as into a body tissue.

Furthermore, the problem mentioned above in the background may be addressed by a structural part with a cannula for the subcutaneous administration of an active substance, whereby the structure is distinguished by the cannula described here.

Manufacturing the structural part with the present cannula imparts a high operating safety to the structural part.

Moreover, the problem mentioned above in the background may be addressed by an insertion head comprising a structural part with a cannula for the subcutaneous administration of an active substance according to the embodiments disclosed herein, and in which the insertion head is distinguished by the structural part or by a receptacle for such a structural part.

If the insertion head has either such a structural part or a receptacle for it, the latter can also be made available. Thus, the invention can be used either in an insertion head for medical or pharmaceutical purposes, which insertion head can be placed on an organic tissue such as human skin. To this end the insertion head comprises the piercing means that penetrates into the tissue when the insertion head is placed on the tissue or optionally also only after the insertion head was placed on the tissue.

So-called transfer sets are frequently used for using administrations of insulin by an insulin pump in order to establish a connection between the insulin pump and a body. A so-called headset, which surrounds the insertion head, is arranged in a hose system of the transfer set and is provided for carrying out the administration of insulin by a needle into the human body. For example, adhesive films are provided for the placing of such insertion heads on the surface of the skin of the human body onto which films the insertion heads can be arranged and that enter an adhesive connection with the skin surface. In order to supply the insulin to the human body the needle is to be withdrawn from the cannula, which is also in the human body, after the concluded piercing procedure so that the insulin can be subsequently supplied via the cannula. To this end a permanent and pressure-proof as well as liquid-tight connection is necessary between the plastic structural part, such as in this embodiment in the form of a cannula housing, which is arranged on the end on the one end of the cannula inside the insertion head and between the end of the cannula. Otherwise, there would be the danger of a false dosing, as a result of too little insulin being injected into the body. Such a danger is prevented in the present embodiment.

Moreover, an exact determination of the position of the cannula relative to the cannula housing is possible during the manufacturing process with the method in accordance with the embodiments of invention, and thus also simplifies an automation of the method.

In present embodiments the needle is pierced through the septum element that covers the cannula. The probability is correspondingly high that the final position of needle and cannula to one another is imprecise. This problem is reinforced even more so by the tendency for the needle to drift when perforating through the septum element. This is especially true in the case of needles or needle tips that are asymmetrically ground.

However, in at least one embodiment of the present disclosure the needle or the piercing means have not yet been threaded onto or in the cannula, which has yet neither been built up nor covered by a septum element. The positioning of the needle and the cannula to one another is accordingly more precise. The insertion of the needle and the cannula takes place only after this threading on. Only afterwards is the septum element pushed from the rear over the needle end.

Also, no additional structural parts for fixing the cannula in the cannula housing are required. In particular, regarding the fixing of the cannula, the carrying out of an ultrasonic connection by an ultrasonic sonotrode or the carrying out of another connection method such as, for example, adhering, in order to fix the cannula in the cannula housing before the placing of the needle and/or of the septum element are not necessary. In the present embodiments such an additional manufacturing step can be eliminated since the cannula and the needle with the cannula housing are molded around. To this extent a saving of time as well as of cost can be additionally achieved in comparison to traditional manufacturing methods.

No subsequent introduction of a piercing means into the cannula is necessary after the completed injection molding of the end of the cannula with the plastic material of the cannula housing due to the already initial arrangement of the piercing means inside the cannula, which has the end construction in the upper area according to the invention. As a result, damage in particular to the upper cannula end or also to the adjacent parts of the cannula housing is prevented. Therefore, a threading of the needle into a cannula is not needed. Due to the avoidance of such a threading-in step, as mentioned above, a rapid and automated production or manufacture of the cannula housing together with the cannula for insertion head can be carried out in accordance with the invention.

In addition, such a manufacture is economical since it on the one hand can be rapidly carried out and on the other hand the presence and introduction of a pin for the arrangement of the cannula inside the cannula housing, as was customary previously in the prior art, is no longer necessary; rather now, instead of the pin, the piercing means is used as guide element in the manufacture. To this extent the problem mentioned above in the background is also solved by using a piercing means as a guide pin for a cannula for the subcutaneous administration of an active substance.

Further advantages, goals and properties of the various embodiments of the present invention are explained using the following description of the attached drawings in which a manufacturing method and a corresponding construction of a structural part for the subcutaneous administration of an active substance and an insertion device to this end are shown by way of example.

FIGS. 1A to 1D explain the essential manufacturing steps 1 to 4 for the production of a structural part 5 (see in particular FIG. 2) with a flexible cannula 6 and an associated cannula housing 7 (see starting from FIG. 1B).

In the first manufacturing step 1, in accordance with FIG. 1A, the flexible cannula 6 is threaded onto a piercing means 8 to form a cannula piercing unit 9, whereby the piercing means 8 is a needle 10 in this exemplary embodiment. The flexible cannula 6 is constructed in this illustrative embodiment as a soft cannula consisting of a polymer material.

On the one hand the tip 11 of the piercing means projects on the front side over a first end area 12 of the flexible cannula 6. On the other hand one end 13 of the piercing means 8 projects on the back side over a second end area 14 of the flexible cannula 6.

The second end area 14 is formed to a funnel 15 in this exemplary embodiment. In so far the shape of the second end area 14 deviates from the cylindrical shape of the rest of the cannula area 16.

In addition, such a funnel-shaped formation of the flexible cannula 6 makes possible the unintended exiting of liquids, such as insulin, between an outer wall of the cannula and between the cannula housing 7 since the funnel shape not only makes available an enlarged inlet opening for the insulin that subsequently flows through the cannula 6 but also make possible a firm connection with the plastic of the cannula housing 7, which plastic surrounds the funnel 15. This has the advantageous result of the connection between a cannula housing 7 and the flexible cannula 6 being able to withstand pressures of up to 4 bar or more without problems in a sealing manner upon the supplying of insulin.

The flexible cannula 6 was threaded in this illustrative embodiment on the funnel side in the direction of the arrow 17 from the front-side tip 11 on to the piercing means 8.

In the second manufacturing step 2, in accordance with FIG. 1B, the flexible cannula 6 is injection molded with another polymer material in the area of the funnel 15, i.e., in the second end area 14 of the flexible cannula 6, so that the cannula housing 7 is injection molded onto the flexible cannula 6 in a liquid-tight and pressure-tight manner.

It can readily be recognized that the funnel 15 forms an undercut 18 that can be surrounded by the other polymer material of the cannula housing 7 so that the flexible cannula 6 is secured against sliding out of the cannula housing 7.

The cannula piercing unit 9 was inserted into a suitable injection-molding tool (not shown) for the special injection molding procedure. The injection molding tool is constructed in such a manner in this illustrative embodiment that the piercing means 8 does not have a firm connection with the cannula housing 7 so that the piercing means 8 penetrates the cannula housing 7 in a movable manner.

In the third manufacturing step 3, in accordance with FIG. 1C, a disk-shaped septum element 19 is set on the end side—that is, over the end 13 of the piercing means 8—onto the piercing means 8 and is pushed into a support lug 20 (see also FIG. 1B) of the cannula housing 7.

The septum element 19 is subsequently flanged by a thermal treatment of the cannula housing area 21 by a bead 22 on the edge so that the septum element 4 is firmly enclosed on the side surface 23 and the top 24 by the edge-side bead 22. This results in an aseptically tight action relative to a chamber 25 to which a liquid active substance such as, for example, insulin, is supplied via a tubular conduit 26 of the cannula housing 7 when the piercing means 8 has been removed during a usage. The liquid active substance passes from the chamber 25 into the flexible cannula 6 and from there, for example, into a human body.

The liquid active substance is supplied to the tubular conduit 26 to this end by a catheter (not shown in detail in this illustrative embodiment), whereby the catheter is connected at a connection position 27 to the cannula housing 7. Thus, the liquid active substance passes in accordance with the supply direction 28 into the cannula housing 7.

In the fourth manufacturing step 4, according to FIG. 1D, another holding device 29 is attached on the back side onto the piercing means 8, that is, on the end 13 of the piercing means 8.

The piercing means 8 can be drawn out of the cannula 6 by the holding device 29 when being used and be rapidly removed in a simple manner, in particular in an automated manner.

The structural part 5 manufactured by the method embodiments in accordance with the invention can be viewed in a clear manner in FIG. 2 regarding its individual components. In addition to the general base forms of the individual components it is also possible to recognize that the flexible cannula 6 by means of the funnel 15 can be threaded onto the piercing means 8 in such a manner that it is secure during operation.

To this extent the funnel 15 can represent a very advantageous threading-in device on the flexible cannula 6 so that the piercing means 8 can be introduced in a purposeful and centered manner into the flexible cannula 6. This creates a simple construction of a centering device. It is understood that such an advantageous centering device or threading-in device is not limited to the funnel shape shown here by way of example.

According to the view of FIG. 3, the assembled and ready-to-use structural part 5 is partially represented again in an enlarged manner in the area of the flexible cannula 6 and of the piercing means 8.

The funnel-shaped second end area 14 of the flexible cannula 6 is approximately equal to a truncated cone designed hollow on the inside. This funnel shape is simple to manufacture in a reshaping method, as well as reshaping in an injection molding method. However, it could be possible due to this simple funnel form that after a very long time the flexible cannula 6 would nevertheless come loose from its seat on the cannula housing.

In order to be able to better exclude even this slight risk, the funnel shape can also be shaped differently, as is shown by way of example with another exemplary embodiment of an alternative and soft cannula 106 in accordance with FIGS. 4 and 5.

As a result of the beaded area 140 on an end area 114 of the soft cannula 106 the funnel 115 there can be better injection-molded by a material of cannula housing 107 so that the soft cannula 106 is once again fixed in an improved manner inside the material of the cannula housing 107. To this extent a separation of the soft cannula 106 out of the cannula housing 107 is virtually completely excluded in this illustrative embodiment.

The piercing means 108 (see FIG. 5) is fixed in radial direction 141 substantially by the soft cannula 106 in this illustrative embodiment. On the other hand, in the axial direction 142 the piercing means 108 is movably supported almost friction-free inside the soft cannula 108.

According to the view in accordance with FIG. 6, a known insertion device 150 with an insertion head 141 can be seen in an inactive state comprising the cannula housing 107 and the soft cannula 108 arranged in it.

A generic holding device 120 is constructed in this illustrative embodiment as a housing element 152 of the insertion device 150.

After a pivoting procedure in the direction of pivoting 153, an application of the insertion head 151 on a tissue and a removal of the piercing means 108 from the soft cannula 106, insulin can be conducted in supply direction 128 into the cannula housing 107.

The insertion device 150 comprises the above-described components and makes possible a pivoting of the cannula housing 170 through 90° in order to make possible a piercing into the tissue, in particular into a skin surface.

The exact manner of the functioning of such an insertion device 150 is sufficiently known from the prior art, for example from the initially mentioned European patent application EP 1 970 091 A1.

Still further exemplary embodiments are provided hereafter.

In one exemplary embodiment, a method for manufacturing a structural part 5 with a cannula 6 for the subcutaneous administration of an active substance is disclosed, in which the cannula 6 is connected to a cannula housing 7, characterized in that the loose cannula 6 is threaded on a piercing means 8 to form a ready-to-use cannula piercing unit 9 and subsequently a cannula housing 7 is injection-molded onto the cannula 6.

In another exemplary embodiment, a method for manufacturing a structural part 5 with a cannula 6 for the subcutaneous administration of an active substance is disclosed, in which the cannula 6 is connected to a cannula housing 7, characterized in that one end of the cannula 6 is formed to an end area 14 that deviates from the shape of the rest of the cannula area 16 and subsequently a cannula housing 7 is injection-molded on this end area 14 of the cannula 6.

In another embodiment, the cannula 6 is threaded on a piercing means 8 to form a ready-to-use cannula piercing unit 9 before the injection-molding of the cannula housing 7.

In another embodiment, the cannula housing 7 is injection-molded on the cannula 6 in such a manner that a piercing means 8 movably penetrates the cannula housing 7.

In another embodiment, a septum element 19 is inserted on the end side of piercing means 8 after the injection molding of the cannula housing 7 and is arranged in a support lug 20 of the cannula housing 7, whereby in particular the septum element 19 is thermally flanged into the support lug 2.

In another embodiment, a holding device 29 is subsequently attached on the end side 13 of a piercing means 8.

In still another embodiment, a cannula 6 for a structural part 5 for the subcutaneous administration of an active substance, for example, on an application part of an insertion head, is disclosed, and is characterized in that the cannula 6 has an end area 14 that deviates from the shape of the rest of the cannula area 16.

In another embodiment, the end area 14 of the cannula 6 and the rest of the cannula area are manufactured in one piece from a single material.

In yet another embodiment, a structural part 5 with a cannula 6 for the subcutaneous administration of an active substance produced in accordance with any one of the methods previously disclosed herein, is characterized in that the structural part 5 comprises a cannula 6 that has an end area 14 that deviates from the shape of the rest of the cannula area 16 and in which the end area 14 of the cannula 6 and the rest of the cannula area are manufactured in one piece from a single material.

In still yet another embodiment, an insertion head 151 comprising a structural part 5 with a cannula 6; 106 for the subcutaneous administration of an active substance is disclosed and is characterized in that the insertion head 151 comprises a structural part 5 or a receptacle for the structural part (5), and in which the structural part 5 comprises a cannula 6 that has an end area 14 that deviates from the shape of the rest of the cannula area 16 and in which the end area 14 of the cannula 6 and the rest of the cannula area are manufactured in one piece from a single material.

What is claimed is:

1. A method for manufacturing a structural part for a subcutaneous administration of an active substance, said method comprising:
   providing a cannula having an end area that deviates from a shape of a rest of a cannula area;
   providing a piercing needle;
   threading the cannula on the piercing needle, wherein after threading the cannula on the piercing needle a part of the piercing needle protrudes from the end area of the cannula; and
   subsequently, injection-molding a cannula housing onto the end area of the cannula, and onto an area of the part of the piercing needle protruding from the end area of the cannula that is adjacent to the end area of the cannula.

2. The method according to claim 1, wherein the piercing needle has a tip; and wherein for threading the cannula on the piercing needle, the tip of the piercing needle is inserted into the end area of the cannula.

3. The method according to claim 1, wherein for injection-molding the cannula housing onto the end area of the cannula and the adjacent area of the piercing needle protruding from the end area of the cannula, the injection-molding is performed in such a manner that the piercing needle movably penetrates the cannula housing.

4. The method according to claim 1, wherein the injection molding of the cannula housing defines a support lug; and said method further comprising inserting a septum element on an end side of the piercing needle after the injection molding of the cannula housing; and arranging the septum element in the support lug of the cannula housing.

5. The method according to claim 4, wherein arranging the septum element in the support lug of the cannula housing is via thermally flanging the septum element into the support lug.

6. The method according to claim 4, further comprising attaching a holding device on the end side of the piercing needle after inserting the septum element.

* * * * *